(12) United States Patent
MacGillivray (10) Patent No.: US 7,524,966 B2
(45) Date of Patent: Apr. 28, 2009

(54) METHOD FOR PREPARING LADDERANES

(75) Inventor: Leonard R. MacGillivray, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 855 days.

(21) Appl. No.: 10/683,472

(22) Filed: Oct. 8, 2003

(65) Prior Publication Data

US 2009/0088572 A1 Apr. 2, 2009

(51) Int. Cl.
*C07D 221/02* (2006.01)
(52) U.S. Cl. ............. 546/255; 204/157.71; 204/157.76; 204/157.81; 204/157.87; 204/157.91
(58) Field of Classification Search ................. 546/255, 546/285; 204/157.71, 157.76, 157.81, 157.87, 204/157.91
See application file for complete search history.

(56) References Cited

U.S. PATENT DOCUMENTS

2004/0014963 A1 1/2004 Atwood et al.
2006/0004217 A1 1/2006 MacGillivray

FOREIGN PATENT DOCUMENTS

| WO | WO 99/16734 | 4/1999 |
| WO | WO 00/63140 | 10/2000 |
| WO | WO 2004/042270 | 5/2004 |
| WO | WO 2005/035473 | 4/2005 |
| WO | WO 2005/124754 | 12/2005 |

OTHER PUBLICATIONS

Li et al., J. Am. Chem. Soc., 1996, 118, 11752-11758.*
MacGillvray et al., J. Am. Chem. Soc. 2000, 122, 7817-7818.*
International Search Report for International Application No. PCT/US2005/020599, mailed Dec. 6, 2005.
Papaefstathiou et al., "An inverted metal-organic framework with compartmentalized cavities constructed by using an organic bridging unit derived from the solid state", *Angew Chem Int Ed*, 41(12), 2070-2073 (2002).
U.S. Appl. No. 11/150,587, filed Jun. 10, 2005, Data Storage Materials.
International Search Report for International Application No. PCT/US2004/033295, mailed Apr. 21, 2005.
Anderson et al., "Templates in Organic Synthesis: Definitions and Roles", F. Diederich, P. S. Stang, Eds.: Wiley-VCH, New York, 1-38 (2000).
Atwood et al., "Storage of Methane and Freon by Interstitial van der Waals Confinement", *Science*, 296, 2367-2369 (2002).
Balzani et al., "The Bottom-Up Approach to Molecular-Level Devices and Machines", *Chem. Eur. J.*, 8, 5524-5532 (2002).
Bassani et al., "Supramolecular Catalysis of Olefin [2+2] Photodimerization", *J. Am. Chem. Soc.*, 122, 8795-8796 (2000).
Damste et al., "Linearly Concatenated Cyclobutane Lipids Form a Dense Bacterial Membrane", *Nature*, 419, 708-712 (2002).
DeLong, "All in the Packaging", *Nature*, 419, 676-677 (2002).
Desiraju, "Crystal Gazing: Structure Prediction and Polymorphism", *Science*, 278, 404-405 (1997).
Drexler, "Molecular Engineering: An Approach to the Development of General Capabilities for Molecular Manipulation", *PNAS*, 78, 5275-5278 (1981).
Drexler, "Machine-Phase Nanotechnology", *Sci. Amer.*, 285, 74-75 (2001).
Eigler et al., "Positioning Single Atoms with a Scanning Tunnelling Microscope", *Nature*, 344, 524-526 (1990).
Friščič et al., "Double Inclusion of Ferrocene within a Doubly Interpenetrated Three-Dimensional Framework Based on a Resorcin[4]arene", *J. Organometallic Chemistry*, 666, 43-48 (2003).
Friščič et al., "Template-switching: A Supramolecular Strategy for the Quantitative, Gram-Scale Construction of a Molecular Target in the Solid State", *Chem. Comm.*, 1306-1307 (2003).
Friščič et al., "Cyclophanes and Ladderanes: Molecular Target for Supramolecular Chemists", *Supramolecular Chemistry*, 17, 47-51 (2005).
Gao et al., "Supramolecular Construction of Molecular Ladders in the Solid State", *Angew. Chem. Int. Ed.*, 43, 232-236 (2004).
Hamilton et al., "Discrete and Infinite Coordination Arrays Derived from a Template-Directed, Solid-State, Organic Synthesis", *CrystEngComm.*, 4, 223-226 (2002).
Hamilton et al., "A Polyhedral Host Constructed Using a Linear Template", *J. Am. Chem. Soc.*, 124, 11606-11607 (2002).
Hecht, "Welding, Organizing, and Planting Organic Molecules on Substrate Surfaces—Promising Approaches Towards Nanoarchitectonics from the Bottom up", *Angew. Chem. Int. Ed. Engl.*, 42, 24-26 (2003).
Hla et al., "Inducing Single-Molecule Chemical Reactions with a UHV-STM: A New Dimension for Nano-Science and Technology", *ChemPhysChem.*, 2, 361-366 (2001).
Hopf et al., "Topochemical Reaction Control in Solution", *Angew. Int. Ed. Engl.*, 34, 685-687 (1995).
Hopf, "Step by Step—From Nonnatural to Biological Molecular Ladders", *Angew. Chem. Int. Ed.*, 42, 2822-2825 (2003).
Kelly et al., "A Bisubstrate Reaction Template", *J. Am. Chem. Soc.*, 111, 3744-3745 (1989).
Kuypers et al., "Anaerobic Ammonium Oxidation by Anammox Bacteria in the Black Sea", *Nature*, 422, 608-611 (2003).

(Continued)

*Primary Examiner*—Bernard Dentz
*Assistant Examiner*—David E Gallis
(74) *Attorney, Agent, or Firm*—Viksnins Harris & Padys PLLP (57) ABSTRACT

Ditopic molecules in the form of linear reaction templates have been used to construct ladder-like hydrocarbons known as [n]-ladderanes (n=3,5). The templates assemble and position reactant molecules in the solid state by way of hydrogen bonds for [2+2] photodimerization. The products, which are based on recently identified naturally occurring frameworks, form stereospecifically, in gram quantities, and in quantitative yield. The control of reactivity achieved using linear templates provides a basis for the development of molecular tools, termed assemblers, that could be used to manufacture, with atomic-level precision, a wide range of products (e.g. molecular nanostructures) with unique properties.

38 Claims, 12 Drawing Sheets

OTHER PUBLICATIONS

Li et al., "Synthesis, Characterization, and Photophysics Studies of Photoactive Chromophore 2-Naphthyl-Labeled [*n*]-Ladderanes" *J. Am. Chem. Soc.*, 118, 11752-11758 (1996).

Lindoy et al., "Mono- and Diformylation of 4-Substituted Phenols: A New Application of the Duff Reaction", *Synthesis*, 1029-1032 (1998).

MacGillivray, "From Engineering Crystals to Engineering Molecules: Emergent Consequences of Controlling Reactivity in the Solid State Using Linear Templates", *CrystEngComm.*, 4, 37-41 (2002).

MacGillivray, "Controlling Molecular Synthesis in the Solid State Using Linear Templates", in "*Strength from Weakness: Structural Consequences of Weak Interactions in Molecular, Supermolecules, and Crystals*" Eds A Domenicano and I Hargittai, 355-365 (2002).

MacGillivray et al., "Toward a Reactant Library in Template-Directed Solid-State Organic Synthesis: Reactivity Involving a Monofunctional Reactant Based on a Stillbazole", *Ind. Eng. Chem. Res.*, 41, 4494-4497 (2002).

MacGillivray, "Supramolecular Control of Reactivity in the Solid State Using Linear Templates", in *Separations and Reactions in Organic Supramolecular Chemistry*, Eds F. Toda and R. Bishop, 185-204 (2004).

MacGillivray et al., "Template-Controlled Synthesis in the Solid-State", *Topics in Current Chemistry*, 248, 201-221 (2004).

Mehta et al., "Characterization of [*n*]-Ladderanes of Unprecedented Length: A New Record for Fused Carbocyclic Arrays", *J. Org. Chem.*, 59, 6131-6132 (1994).

Nicolaou et al., "The Art and Science of Total Synthesis at the Dawn of the Twenty-First Century", *Angew. Chem. Int. Ed.*, 39, 44-122 (2000).

Papaefstathiou et al., "Inverted Metal-Organic Frameworks: Solid-State Hosts with Modular Functionality", *Coordinated Chemistry Reviews*, 246, 169-184 (2003).

Papaefstathiou et al., "Directed Assembly and Reactivity of Olefins within a One-Dimensional Ladder-Like Coordination Polymer Based on a Dinuclear Zn(II) Platform", *Chem Commun.*, 3974-3976 (2005).

Rekharsky et al., "Ion-Pairing Molecular Recognition in Water: Aggregation at Low Concentrations that is Entropy-Driven", *J. Am. Chem. Soc.*, 124, 14959-14967 (2002).

Schmidt, "Photodimerization in the Solid State", *Pure Appl. Chem.*, 27, 647-678 (1971).

Warrener et al., "A Tandem Cycloaddition Protocol for the Controlled Synthesis of [*n*]Ladderanes: New Rods and Spacers", *J. Am. Chem. Soc.*, 116, 3645-3646 (1994).

Whitesides, "The Once and Future Nanomachine", *Sci. Amer.*, 285, 78-83 (2001).

Williams et al., "How Can Enzymes be so Efficient?", *Chem. Commun.*, 1973-1976 (2003).

* cited by examiner

[3]-ladderane
*n* = 3

[5]-ladderane
*n* = 5

Figure 5

METHOD FOR PREPARING LADDERANES

GOVERNMENT FUNDING

The invention described herein was made with government support under CAREER Award, DMR-0133138, L.R.M. awarded by the National Science Foundation. The United States Government has certain rights in the invention.

BACKGROUND OF THE INVENTION

Tools that enable picking and positioning of individual atoms and molecules for chemical reaction could have widespread applications in chemical synthesis and materials science (e.g. molecular nanotechnology). Such tools, or assemblers, could combine the chemical diversity of synthetic organic chemistry (e.g. functional groups), which is chiefly realized at the atomic level, with the ability of human engineers to fabricate objects using mechanical devices (e.g. robotic welders), which is chiefly realized at the macroscopic level, for the development of a universal molecular manufacturing scheme. See K. E. Drexler, *Proc. Natl. Acad. Sci. USA* 78, 5275 (1981); K. E. Drexler, Sci. Amer. 285, 74 (2001); G. M. Whitesides, *Sci. Amer.* 285, 78 (2001); K. C. Nicolau, D. Vourloumis, N. Winssinger, P. S. Baran, *Angew. Chem. Int. Ed. Engl.* 39, 44 (2000); S. Hecht, *Angew. Chem. Int. Ed. Engl.* 42, 24 (2003); and K. E. Drexler, *Nanosystems. Molecular Machinery, Manufacturing and Computation*; Wiley-Interscience: New York (1992).

Owing to the superior stereo- and regiocontrol of chemical synthesis offered by assemblers, molecular manufacturing via molecular assemblers could provide efficient, low-cost access to molecules, and materials, with unique molecular (e.g. catalytic) and bulk physical (e.g. mechanical) properties. Despite this realization, however, a synthetic system that enables such general 'pick-and-place' control of atoms and molecules has not been realized.

Top-down approaches, which have employed surface microscopy tips (e.g. STM) to position reactive sites mechanically, have had difficulties achieving atomic-level dexterity and high throughput for grabbing individual molecules and manufacturing appreciable amounts of product, respectively. See S. Hecht, *Angew. Chem. Int. Ed. Engl.* 42, 24 (2003); V. Balzani, A. Credi, M. Venturi, *Chem. Eur. J.* 8, 5525 (2002); D. M. Eigler and E. K. Schweizer, *Nature* 344, 594 (1990); and S.-W. Hla, G. Meyer, K.-H. Rieder, *ChemPhysChem.* 2, 361 (2001).

Bottom-up approaches, which have employed molecules to recognize and assemble reactive sites chemically, have had difficulties contending with structure effects of entropy and solvent of the liquid phase, which can hinder reactants molecules from achieving the necessary order for reaction. See V. Balzani, A. Credi, M. Venturi, *Chem. Eur. J.* 8, 5525 (2002); J.-M. Lehn, *Supramolecular Chemistry*; Wiley-VCH: Weinheim (1995); T. R. Kelly, C. Zhao, G. J. Bridger, *J. Am. Chem. Soc.* 111, 3744 (1989); and D. M. Bassani, V. Darcos, S. Mahony, J.-P. Desvergne, *J. Am. Chem. Soc.* 122, 8795 (2000).

A [n]-ladderane is a molecule that consists of n edge-sharing cyclobutane rings (where $n \geq 2$) that define a molecular equivalent of a macroscopic ladder. See H. Hopf, *Angew. Chem.* 2003, 115, 2928-2931; and *Angew. Chem., Int. Ed.* 2003, 42, 2822-2825. Ladderanes are considered promising building blocks in optoelectronics and, very recently, have been identified in biological systems (where: n=3 and 5), in the form of ladderane lipids, being integral components in the microbiological conversion of ammonium and nitrite to dinitrogen gas. See W. Li, M.A. Fox, *J. Am. Chem. Soc.* 1996, 118, 11752-11758; J.S. S. Damste, et al., *Nature* 2002, 419, 708-712; E. F. DeLong *Nature* 2002, 419, 676-677; and M. M. M. Kuypers, et al., *Nature* 2003, 422, 608-611.

In the simplest case, a cis-fused [n]-ladderane (n=3, 5, 7 . . . ) can be constructed by photochemical dimerization of two all-trans-poly-m-enes (m=2, 3, 4.). Despite the apparent simplicity of this intermolecular process, however, such a transformation generally fails. This can be attributed to the lack of a method that overcomes the energetic cost, due to solvent and entropy effects, of organizing two polyene molecules in a suitable geometry in the liquid phase for photoreaction, although a covalent linker that holds two polyene chains in a parallel orientation for a high-yield, intramolecular photoaddition to give a [n]-ladderane (where: n=3 and 5) has been reported. See H. Hopf, *Angew. Chem.* 2003, 115, 2928-2931; and *Angew. Chem., Int. Ed.* 2003, 42, 2822-2825; D. H. Williams, E. et al., *Chem. Commun.* 2003, 1973-1976; M. Rekharsky, et al., *J. Am. Chem. Soc.* 2002, 124, 14959-14967; and H. Hopf, et al., *Angew. Chem.* 1995, 107, 742-744; *Angew. Int. Ed. Engl.* 1995, 34, 685-687.

Unfortunately, the study of these unique molecules and their properties has been hampered because existing methods for preparing ladderanes typically provide low yields and/or mixtures of products that are difficult to separate. Accordingly, there is currently a need for improved methods and intermediates that can be used to prepare ladderanes. In particular, there is a need for methods that provide improved yields of ladderanes and for methods that provide pure ladderane products as opposed to mixtures of compounds.

SUMMARY OF THE INVENTION

The invention provides template controlled methods for preparing ladderanes. The methods of the invention allow ladderanes of high purity to be prepared in useful quantities (e.g. gram quantities). The invention also provides intermediates useful for preparing ladderanes according to the methods of the invention.

Accordingly, the invention provides a method for preparing a ladderane comprising, associating polyene molecules with a template such that the polyene molecules are properly aligned to allow for formation of the ladderane, and reacting the polyene molecules under conditions suitable to provide the ladderane.

The invention also provides a kit comprising packaging material and at least about 0.5 grams of a ladderane. In one embodiment the kit comprises at least about 1 gram of a ladderane. In another embodiment the kit comprises at least about 2 grams or about 5 grams of a ladderane.

The invention also provides a composition comprising polyene molecules associated with a template such that the polyene molecules are properly aligned to allow for formation of a ladderane. For example, the composition can be a solid (e.g. a crystalline solid).

The invention also provides a ladderane prepared by a method of the invention, as well as a composition comprising at least about 0.5 grams of a ladderane, which composition is prepared according to a method of the invention.

BRIEF DESCRIPTION OF THE FIGURES

FIG. 1. Perspectives of the X-ray crystal structures of the solid-state assemblies: (a) ORTEP view of the assembly 2(5-OMe-res).2(poly-2-ene), (b) ORTEP view of the assembly 2(5-OMeres) 2(poly-3-ene), (c) space-filling view of the packing of 2(5-OMe-res).2(poly-2-ene), and (d) space-filling view of the packing of 2(5-OMe-res).2(poly-3-ene). Selected interatomic distances (Å) and angles (o): O(1) . . . N(1) 2.761(3), O(2) . . . N(2)i 2.736(3), O(1)-H(10) . . . N(1) 175.6(1), O(2)-H(20) . . . N(2)i 172.1(1); (b) O(1) . . . N(1) 2.792 (5), O(2) . . . N(3) 2.777 (6), O(4) . . . N(2)I 2.782(6), O(5) . . . N(4) 2.756 (6), O(1)-H(10) . . . N(1) 173.6(3), O(2)-H(20) . . . N(3) 173.4(3), O(4)-H(40) . . . N(2) 176.6(3), O(5)-H(50) . . . N(4) 175.1(3). Symmetry operator i: −x+1, −y, −z+2. It is noted that the asymmetric units of 2(5-OMe-res).2(poly-2-ene) and 2(5-OMe-res).2(poly-3-ene) are occupied by two full assemblies, which are virtually identical, and one half assembly, which sits around a crystallographic center of inversion, respectively.

FIG. 2. $^1$H NMR spectra of the solid-state assemblies before and after photoreaction: (a) 2(5-OMe-res).2(poly-2-ene) (before), (b) 2(5-OMe-res).2(poly-2-ene) (after), (c) 2(5-OMeres) 2(poly-3-ene) (before), and (d) 2(5-OMe-res).2 (poly-3-ene) (after). Key: filled circle=olefin, cross=cyclobutane.

FIG. 3. ORTEP perspectives of the ladderanes: (a) [3]-ladderane and (b) [5]-ladderane. Symmetry operator ii: −x+2, −y, −z+1. It is noted that the asymmetric units of the [3]-ladderane and [5]-ladderane are occupied by two full ladderanes, which are virtually identical, and one half ladderane, which sits around a crystallographic center of inversion, and an included benzene, respectively.

DETAILED DESCRIPTION

Figure 5:
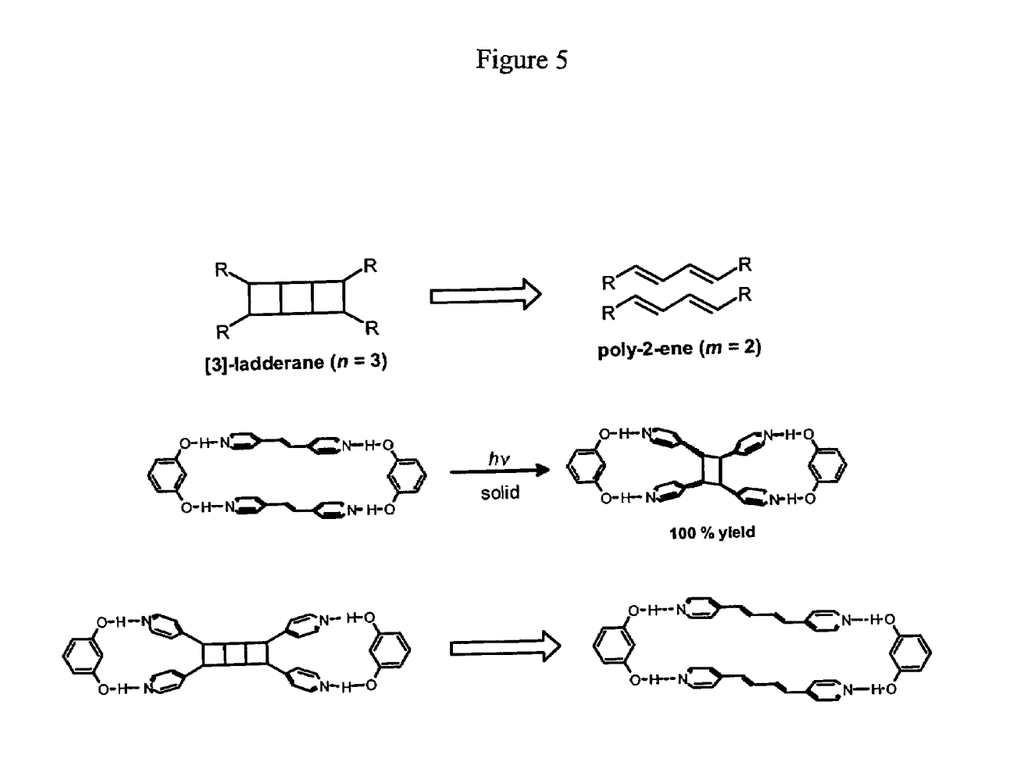
FIG. 5. Illustrates the synthesis and retro-synthesis of [3]-ladderane and [5]-ladderane using resorcinol templates.

That a [n]-ladderane may serve a target of a linear template synthesis is realized by a retrosynthetic analysis of the ladderane framework (FIG. 5). A single-step construction of a [n]-ladderane, which is composed of n linearly fused cyclobutane units, can be achieved by cross-linking two identical all-trans-poly-m-enes (m=2, 3, 4 . . . ) via intermolecular [2+2] photodimerizations. Despite the apparent simplicity of this process, such a transformation has not been reported. This may be attributed to the lack of a suitable method to organize two polyenes, in either solution or the solid state, in a position favorable for ladderane formation. See Mehta, M. B. et al., *J. Org. Chem.* 59, 6131 (1994); R. W. Warrener, et al., *J. Am. Chem. Soc.* 116, 3645 (1994); W. Li and M. A. Fox, *J. Am. Chem. Soc.* 118, 11752 (1996); and H. Hopf, H. Greiving, P. G. Jones, P. Bubenitschek, *Angew. Chem. Int. Ed. Engl.* 34, 685 (1995).

Templates

Figure 4:
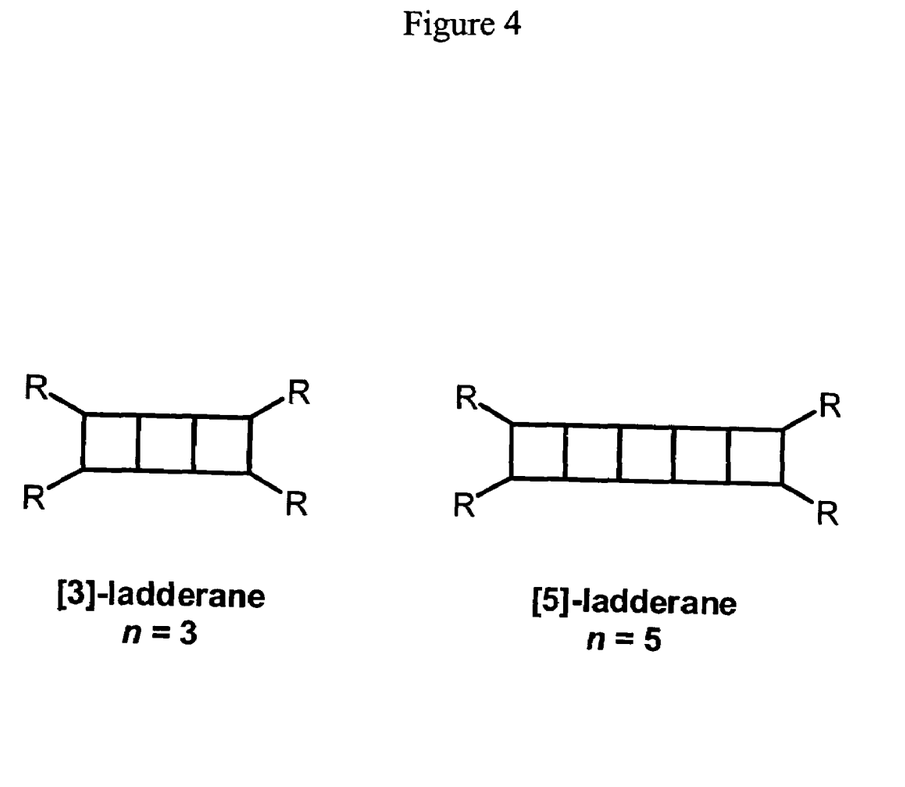
FIG. 4. Illustrates the structure of [3]-ladderane and [5]-ladderane.

Template molecules (e.g. ditopic molecules in the form of linear reaction templates) can be used to construct [n]-ladderanes (see FIG. 4). For related discussions see S. Anderson, H. L. Anderson, In *Templated Organic Synthesis*; F. Diederich, P. S. Stang, Eds.: Wiley-VCH: New York, pp. 1-38 (2000); G. R. Desiraju, *Science* 278, 404 (1997); J. L. Atwood, L. J. Barbour, A. Jerga, *Science* 296, 2367 (2002); G. Mehta, M. B. Viswanath, A. C. Kunwar, *J. Org. Chem.* 59, 6131 (1994); and R. W. Warrener, G. Abbenante, C. H. L. Kennard, *J. Am. Chem. Soc.* 116, 3645 (1994). For example, the linear templates can operate by positioning the two poly-m-enes (e.g. m=2 or 3), via hydrogen bonds for ultraviolet-(UV) induced [2+2]cycloaddition reactions. See G. M. J. Schmidt, *Pure Appl. Chem.* 27, 647 (1971). By using the organized, solvent-free environment of the solid state as the medium for reaction, the effects of entropy and solvent that have made intermolecular interactions of the bottom-up approach difficult to control in the liquid phase can be circumvented. See T. R. Kelly, C. Zhao, G. J. Bridger, *J. Am. Chem. Soc.* 111, 3744 (1989); and D. M. Bassani, V. Darcos, S. Mahony, J.-P. Desvergne, *J. Am. Chem. Soc.* 122, 8795 (2000).

The template can be any inorganic molecule (e.g. a transition metal complex), organic molecule (e.g. a polyol, a polyether, or a polyamine), solid support, or assembly of inorganic and/or organic molecules held together by non-covalent bonds (e.g. a coordination complex) that is capable of associating with the polyenes such that the polyenes are properly aligned to allow for formation of the ladderane. In one embodiment the template comprises an aromatic ring. In another embodiment the template comprises an aromatic ring that is 1,3 substituted with groups capable of associating with the polyene molecules (e.g. a 1,3-substituted phenyl ring or a 1,3-substituted naphthyl ring).

In a preferred embodiment the template is resorcinol (1,3-dihydroxybenzene) or a substituted resorcinol. For example, the template can be resorcinol substituted with one or more (e.g. 1, 2, or 3) $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, cyano, halo, hydroxy, nitro, carboxy, trifluoromethyl, trifluoromethoxy, methylenedioxy, aryl, heteroaryl, aryl$(C_1-C_6)$alkyl, heteroaryl$(C_1-C_6)$alkyl, aryl$(C_1-C_6)$alkanoyl, heteroaryl$(C_1-C_6)$alkanoyl, or NRR, wherein each R is independently $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, and wherein each aryl or heteroaryl is optionally substituted with one or more (e.g. 1, 2, 3, or 4) $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, cyano, halo, nitro, carboxy, trifluoromethyl, trifluoromethoxy, methylenedioxy, or NRR.

Specific and preferred values listed below for radicals, substituents, and ranges, are for illustration only; they do not exclude other defined values or other values within defined ranges for the radicals and substituents A specific resorcinol that can be used as a template according to the methods of the invention is resorcinol, orcinol [5-methylresorcinol], 4-ethylresorcinol, 4-hexylresorcinol, olivetol [5-pentylresorcinol], 4-cyclohexylresorcinol, 4-benzylresorcinol, 4-chlororesorcinol, 4-bromoresorcinol, 4,6-dichlororesorcinol, 4,6-dibromoresorcinol, 4,6-di-tert-butylresorcinol, 4,6-di-(1,1-diphenylethyl)resorcinol, 3,5-dihydroxybenzaldehyde, 5-cyanoresorcinol, 5-acetylresorcinol, 5-methoxyresorcinol, 5-carboxymethylresorcinol, 1,3-dihydroxynaphthalene, 4,6-dibromo-5-carboxymethylresorcinol, 2,4,6-trihydroxybenzaldehyde (phloroglucinaldehyde), methyl 2, 4-6-trihydroxyphenyl ketone, ethyl 2, 4-6-trihydroxyphenyl ketone, propyl 2, 4-6-trihydroxyphenyl ketone, butyl 2, 4-6-trihydroxyphenyl ketone, pentyl 2, 4-6-trihydroxyphenyl ketone, hexyl 2, 4-6-trihydroxyphenyl ketone, or phenyl 2, 4-6-trihydroxyphenyl ketone.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Association Between Templates and Polyenes

According to the methods of the invention, the polyene molecules can be "associated" to the template molecules by any suitable attractive force, such as, for example, ionic bonds, or other non-covalent bonds (e.g. dipole-dipole interactions, hydrogen bonds, van der Waals interactions, or coordination). The term "associated" does not include covalent bonding between the polyene molecules and the template.

Polyenes of any length can be used in the methods of the invention, provided they are capable of forming ladderanes. In one embodiment, the polyene molecules comprise about 3-20 double bonds. In another embodiment, the polyene molecules comprises 3-12 double bonds. In yet another embodiment, the polyene molecules comprises 3-6 double bonds. In yet another embodiment, the polyene molecules comprise only trans double bonds. In yet another embodiment, the polyene molecules comprise only cis double bonds. In yet another embodiment, the polyene molecules comprise a mixture of cis and trans double bonds. The polyenes can be branched or unbranched and they can include other functionality such as rings, heteroatoms and substituents, provided the other functionality does not interfere with the association of the polyenes with the templates or with the reaction to form ladderanes. Typically the polyene molecules comprises from about 6 to about 40 carbon atoms. In one embodiment, the polyene molecules comprises from about 6 to about 30 carbon atoms. In another embodiment the polyene molecules comprises from about 6 to about 20 carbon atoms.

In one embodiment, each polyene is terminally substituted with a group that is capable of associating with the template. For example, each group can independently comprises an amino nitrogen, a thiol, an alcohol, or a carboxylic acid. In one embodiment, each polyene is terminally substituted with a pyridine ring (e.g. a 4-pyridine ring).

Typically, according to the methods of the invention, the polyene double bonds will be aligned within about 3.2 to 4.5 Angstroms of each other in order to facilitate formation of the ladderane. In one particular embodiment, the polyene double bonds are aligned within less than about 4.2 Angstroms of each other.

Reaction

The reaction of the polyenes can be carried out under any conditions that are suitable to allow for the formation of the ladderane. Typically, the reaction is carried out in a solid state (e.g. a crystalline state). The reaction of the polyenes can be initiated using any suitable means. For example, the reaction can conveniently be initiated with an energy source, such as heat or light.

SPECIFIC EMBODIMENTS

The following specific embodiments are for illustration only; they are not limiting and they do not exclude other embodiments described herein.

In one specific embodiment, the invention provides a method for preparing a ladderane comprising, 1) associating two polyene molecules with a template, 2) forming a solid comprising the template and the polyene molecules, wherein the polyene molecules are properly aligned within the solid to allow for formation of the ladderane, and 3) reacting the polyene molecules under conditions suitable to provide the ladderane.

In another specific embodiment, the invention provides a method for preparing a ladderane comprising, 1) associating two polyene molecules with a template comprising two hydroxyl groups, 2) forming a solid comprising the template and the polyene molecules, wherein the polyene molecules are properly aligned within the solid to allow for formation of the ladderane, and 3) reacting the polyene molecules under conditions suitable to provide the ladderane.

In another specific embodiment, the invention provides a method for preparing a ladderane comprising, 1) associating two polyene molecules that each comprise an amino nitrogen with a template comprising two hydroxyl groups, 2) forming a solid comprising the template and the polyene molecules, wherein the polyene molecules are properly aligned within the solid to allow for formation of the ladderane, and 3) reacting the polyene molecules under conditions suitable to provide the ladderane.

In another specific embodiment, the invention provides a method for preparing a ladderane comprising, 1) associating two polyene molecules that each comprise a pyridine ring with a template comprising a 1,3-dihydroxy substituted phenyl ring, 2) forming a solid comprising the template and the polyene molecules, wherein the polyene molecules are properly aligned within the solid to allow for formation of the ladderane, and 3) reacting the polyene molecules under conditions suitable to provide the ladderane.

In another specific embodiment, the invention provides a method for preparing a ladderane comprising, 1) combining polyene molecules that comprise a pyridine ring with template molecules that comprise a 1,3-dihydroxy substituted phenyl ring in a solvent, 2) allowing a crystalline solid that comprises the template molecules and the polyene molecules to form, wherein the polyene molecules are properly aligned within the crystalline solid to allow for formation of the ladderane, and 3) irradiating the solid under conditions suitable to provide the ladderane.

In another specific embodiment, the ladderane is an [n]-3, [n]-4, [n]-5, [n]-6, [n]-7, [n]-8, [n]-9, [n]-10, [n]-11, or [n]-12 ladderane.

In another specific embodiment, the polyene is 1,4-bis(4-pyridyl)-1,3-butadiene or 1,6-bis(4-pyridyl)-1,3,5-hexatriene.

In another specific embodiment, the polyene comprises all cis double bonds.

In another specific embodiment, the polyene comprises all trans double bonds.

In another specific embodiment, the polyene comprises a mixture of cis and trans double bonds.

In another specific embodiment, the template is 1,3-dihydroxybenzene.

EXAMPLES

The invention will now be illustrated by the following non-limiting Examples.

Ladderanes were prepared by co-crystallization of a template molecule (e.g. resorcinol), with an all-trans-bis(4-pyridyl)poly-m-ene (4-pyr-poly-m-ene) to produce a four-component molecular assembly, 2(resorcinol).2(4-pyr-poly-m-ene) (FIG. 5), wherein each resorcinol positioned, by way of two O—H . . . N hydrogen bonds, two polyenes for [2+2] photoreaction. The two polyenes were positioned by the templates such that the carboncarbon double (C=C) bonds of the olefins were parallel and separated by less than about 4.2 Å, a position suitable for reaction. See G. M. J. Schmidt, *Pure Appl. Chem.* 27, 647 (1971). UV-irradiation of the solid produced the [n]-ladderane, the C=C bonds reacting to form the fused cyclobutane framework.

In a typical experiment, one equivalent of the template 5-methoxyresorcinol (5-OMe-res), was co-crystallized with an equimolar amount of a a poly-m-ene (m=2 or 3), from ethanol. Single-crystals of 2(5-OMe-res).2(4-pyr-poly-m-ene) suitable for X-ray analysis formed within the ethanolic solution within a period of approximately one day.

Single-crystal X-ray structure analyses of 2(5-OMe-res).2 (poly-2-ene) and 2(5-OMeres) 2(poly-3-ene) revealed that the templates organized each polyene in a position for intermolecular [2+2] photodimerization favorable for ladderane formation. In each case, the templates and the polyenes formed four-component molecular assemblies held together by four O—H . . . N hydrogen bonds (FIG. 1) wherein the templates oriented the polyenes in a parallel arrangement, the average separation between the stacked C=C bonds ranging from 3.78-3.82 Å in 2(5-OMe-res).2(poly-2-ene) and from 3.69-3.97 Å in 2(5-OMeres) 2(poly-3-ene). Nearest-neighbor assemblies of each solid packed antiparallel such that the olefins of the hydrogen-bonded assemblies are the sole C=C bonds organized to undergo reaction.

To evaluate the reactivity of the solid-state assemblies, powdered crystalline samples of 2(5-OMe-res).2(poly-2-ene) and 2(5-OMe-res).2(poly-3-ene) were subjected to UV-irradiation (broadband Hg lamp). As evidenced by $^1$H NMR spectroscopy (solvent: DMSO-d6), the [3]- and [5]-ladderanes formed stereospecifically and in quantitative yield (FIG. 2). Each ladderane is characterized by the complete disappearance of the olefinic protons and the emergence of cyclobutane protons in the 3.0-4.3 ppm range. The three fused cyclobutane rings of the [3]-ladderane produced two broad signals at 3.49 and 4.30 ppm (ratio: 1:1), while the five fused cyclobutane rings of the [5]-ladderane produced three broad signals at 3.12, 3.29, and 4.26 ppm (ratio: 1:1:1). To confirm the structures of the ladderanes, the reactions were repeated in gram quantities. The templates were then separated from each product via solvent extraction. Single crystals of each product were grown, during a period of approximately three days, by way of slow solvent evaporation from benzene.

Figure 1A:
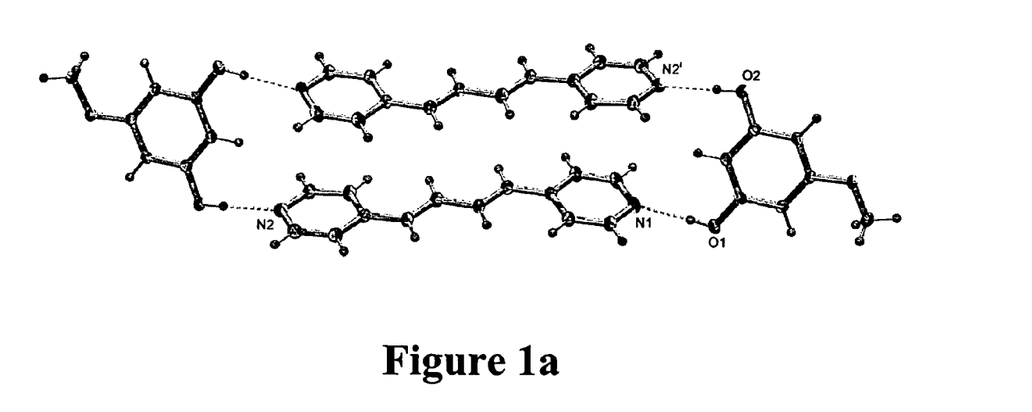
Figure 1B:
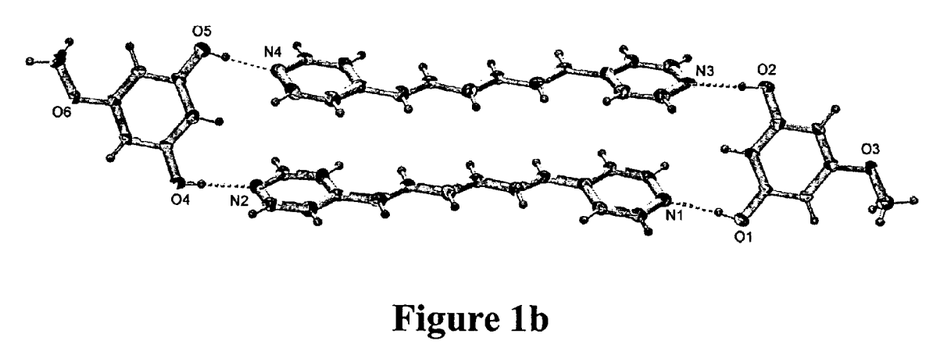
Figure 1C:
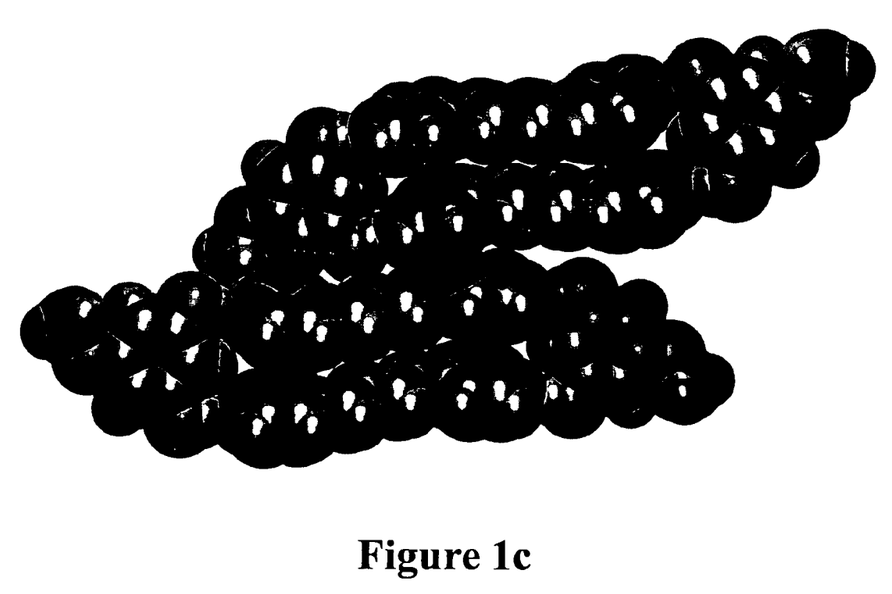
Figure 1D:
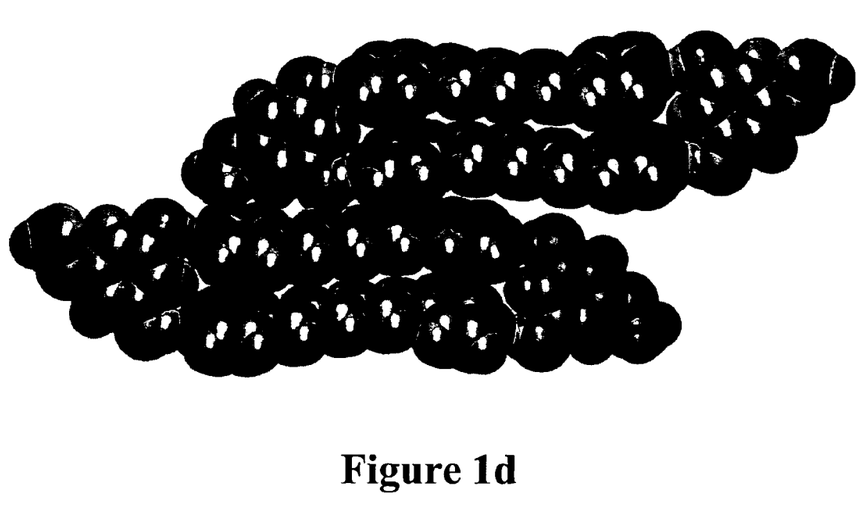
Figure 2A:
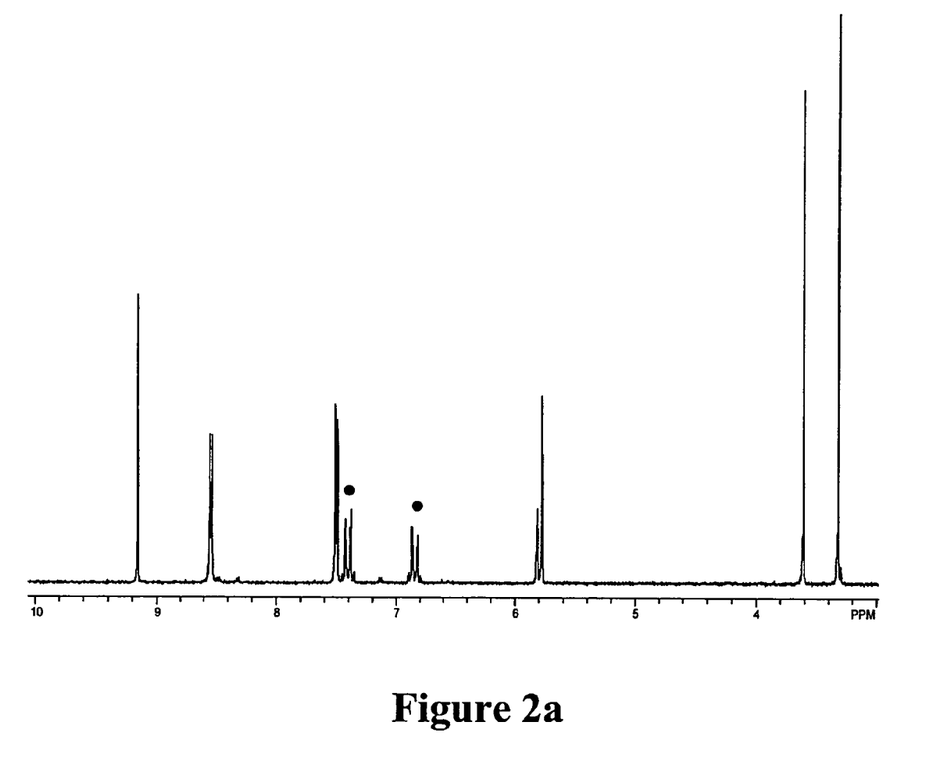
Figure 2B:
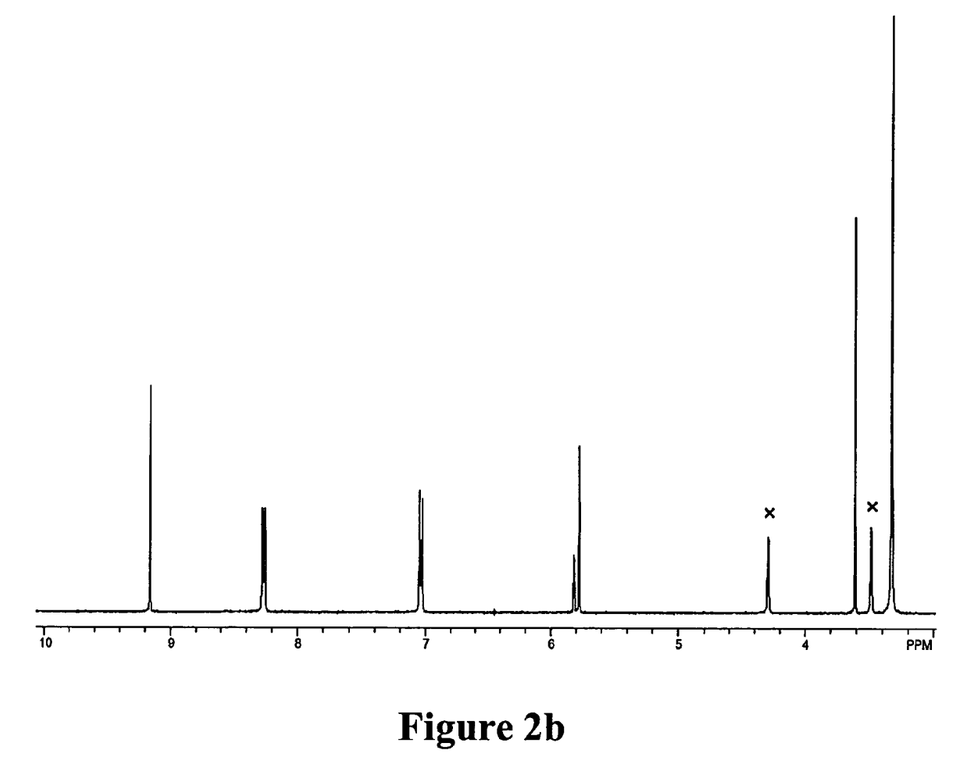
Figure 2C:
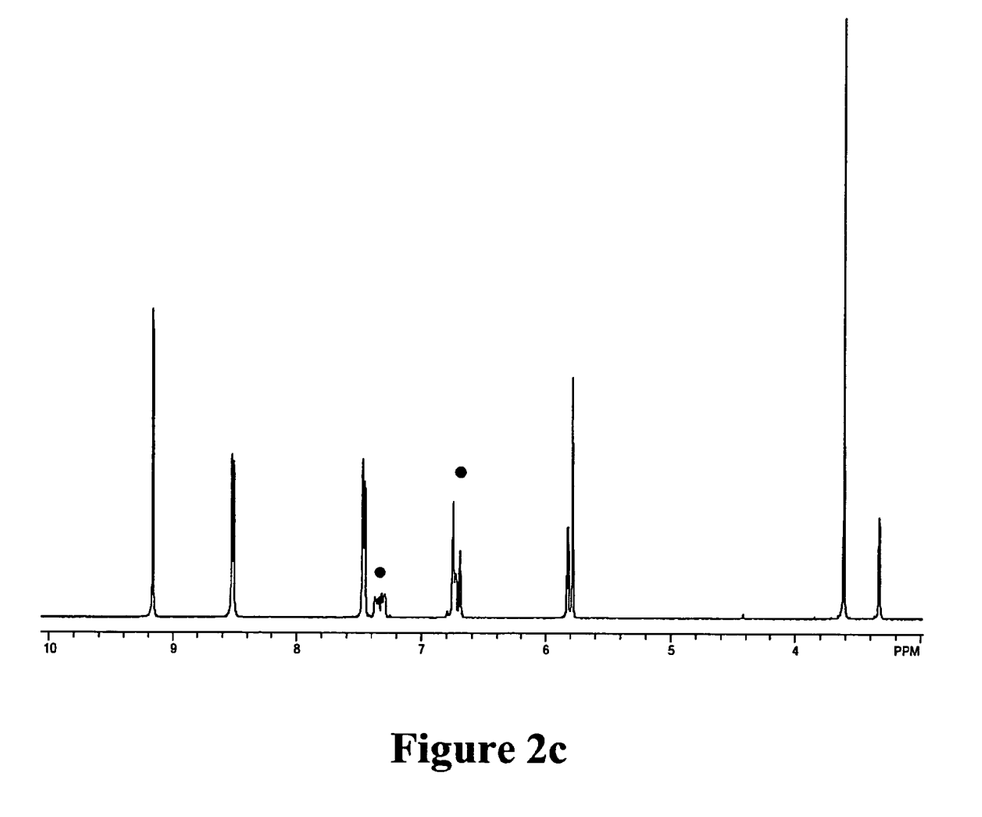
Figure 2D:
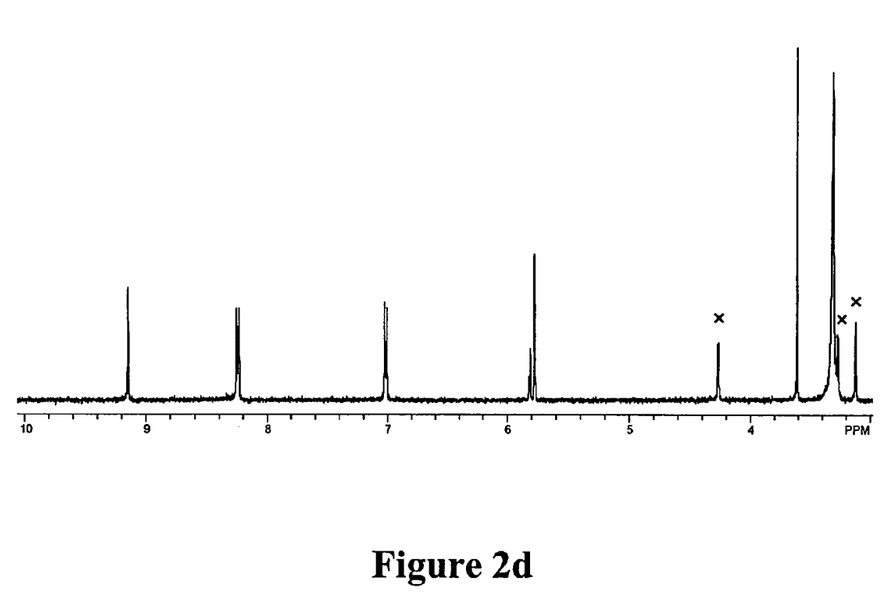
Figure 3A:
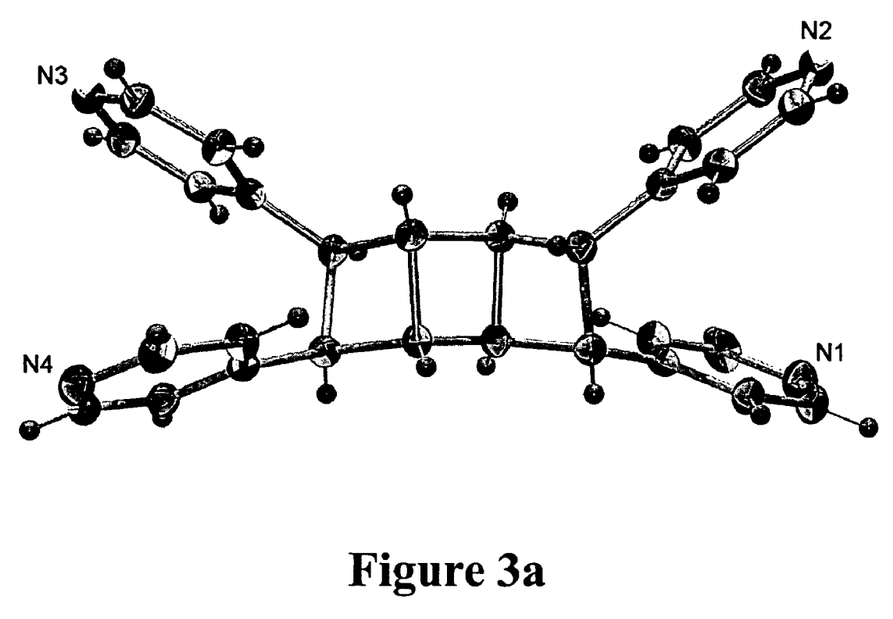
Figure 3B:
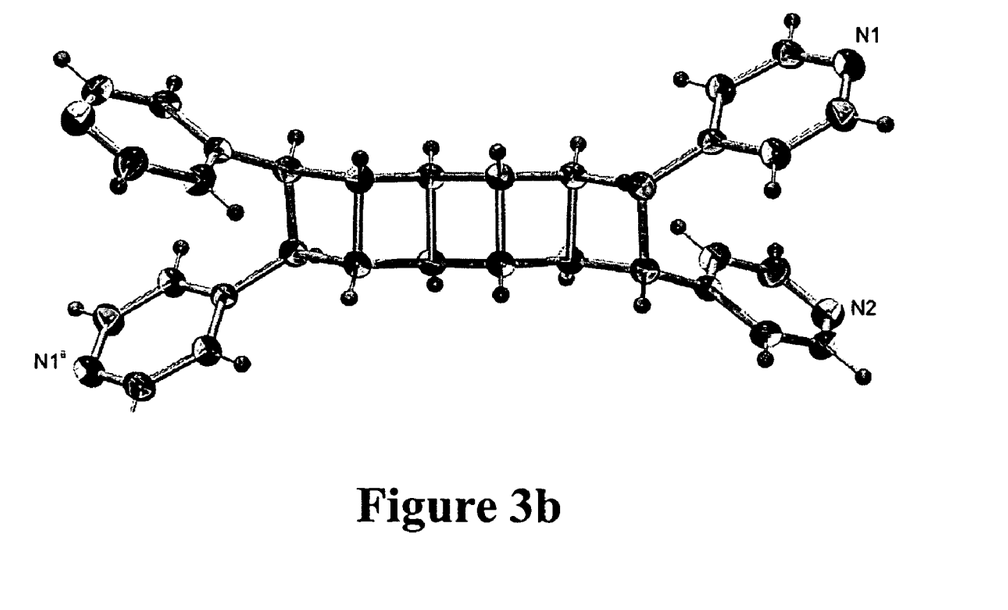

Single-crystal X-ray structure analyses confirm the structures of the ladderanes (FIG. 3). Each product consists of an exo,exo-fused cyclobutane framework with ends functionalized with four 4-pyridyl groups. The C—C bond distances and C—C—C bond angles of the cyclobutane units compare well to both calculated and experimentally related structures. See M. A. Miller and J. M. Schulman, *J. Mol. Struct.* 163, 133 (1988).

The ladderanes appear to form within 2(5-OMe-res).2 (poly-2-ene) and 2(5-OMeres).2(poly-3-ene) by way of stepwise [2+2] photodimerizations. 1H NMR spectra obtained 24 and 48 hours into each reaction reveal that lower-order ladderanes form during the generation of each final product. Thus, a product consistent with a single cycloaddition (i.e. '[1]-ladderane') precedes the [3]-ladderane while products consistent with single and double cycloadditions (i.e. [3]-ladderane) precede the [5]-ladderane. Such stepwise reactions may occur either randomly or by way of a 'zipper' process in each solid.

Thus, templates can be used to construct [n]-ladderanes (n=3 or 5). The templates operate (e.g. in the solid state) by positioning (e.g. by way of hydrogen bonds) polyenes suitable for [2+2] photodimerizations. The ladderanes can be formed in gram quantities and quantitative yield.

All crystal data were measured on a Nonius Kappa CCD single-crystal X-ray diffractometer at liquid nitrogen temperature. After anisotropic refinement of all non-hydrogen atoms, aromatic, methine, and hydroxyl hydrogen atoms were placed in idealized positions and allowed to ride on the atom to which they are attached. All crystallographic calculations were conducted using SHELXL-97 locally implemented on an IBM compatible pentium-based PC (G.M. Sheldrick, SHELXL-97, Program for Refinement of Crystal Structure, University of Göttingen, Göttingen, Germany, 1997.).

Example 1

Preparation of 2(5-OMe-res).2(poly-2-ene)

4-Pyr-poly-2-ene was prepared according to a literature procedure (see P. Carsky, et al., *Liebigs Ann. Chem.* 1980, 291-304). 5-OMe-res was commercially available. Co-crystals of 2(5-OMe-res).2(poly-2-ene) were obtained by evaporation of a solution of 0.058 g of 4-pyr-poly-2-ene (0.28 mmol) and 0.039 g of 5-OMe-res (0.28 mmol) in 3.0 mL of hot methanol. $^1$H NMR of 2(5-OMe-res).2(poly-2-ene) before irradiation (300 MHz, DMSO-d$_6$): δ=9.15 (br. s, 2H), 8.54 (dd, 4H), 7.50 (dd, 4H), 7.40 (dd, 4H), (dd, 4H), 5.82 (br. t, 1H), 5.78 (br. d, 2H), 3.61 (s, 3H). Crystal data for 2(5-OMe-res).2(poly-2-ene): monoclinic, P 2$_1$/c, a=9.182(5) Å, b=13.381(5) Å, c=15.122(5) Å, p=106.712(5)°, V=1779.5 (13) Å$^3$, Z=4, $\rho_{calc}$=1.300 g/cm$^3$, R$_1$=0.0441 for 2324 reflections with I>2σ(I).

Example 2

Preparation of 2(5-OMe-res) 2(poly-3-ene)

4-Pyr-poly-3-ene was prepared according to a literature procedure (see P. Carsky, et al., *Liebigs Ann. Chem.* 1980, 291-304). Co-crystals of 2(5-OMe-res).2(poly-3-ene) were obtained in a manner similar to that described in Example 1 using 0.030 g of 4-pyr-poly-3-ene (0.13 mmol) and 0.018 g of 5-OMe-res (0.13 mmol). $^1$H NMR of 2(5-OMe-res).2(poly-3-ene) before irradiation (300 MHz, DMSO-d$_6$): δ=9.16 (br. s, 2H), 8.52 (dd, 4H), 7.46 (dd, 4H), 7.33 (m, 2H), 6.72 (m, 4H), 5.82 (br. t, 1H), 5.79 (br. d, 2H), 3.61 (s, 3H). Crystal data for 2(5-OMe-res).2(poly-3-ene): triclinic, P$\bar{1}$, a=9.081(3) Å, b=21.143(4) Å, c=21.308(18) Å, α=87.92(4)°, β=79.47(6)°, γ=78.91(2)°, V=3947(4) Å$^3$, Z=2, $\rho_{calc}$=1.260 g/cm$^3$, R$_1$=0.0891 for 6150 reflections with I>2σ(I).

Example 3

Irradiation of 2(5-OMe-res).2(poly-2-ene) to Provide [3]-Laddarane

A finely ground sample of 2(5-OMe-res).2(poly-2-ene) was placed between two pyrex plates and irradiated with a 500 W Hg lamp. The sample was turned in eight hour intervals to ensure uniform irradiation over a period of 120 hours to provide the [3]-ladderane in 100% conversion. $^1$H NMR of irradiated 2(5-OMe-res).2(poly-2-ene) (300 MHz, DMSO-d$_6$): δ=9.16 (br. s, 4H), 8.26 (dd, 8H), 7.04 (dd, 8H), (br. t, 2H), 5.78 (br. d, 4H), 4.30 (br. s, 4H), 3.61 (s, 6H), 3.49 (br. s, 4H). Stirring of the irradiated solid with 1M KOH solution, followed by extraction with methylene chloride and evaporation of the organic phase, yielded the [3]-ladderane as a white solid in 85% yield. Crystal data for the [3]-ladderane: triclinic, P$\bar{1}$, a=12.534(5) Å, b=12.583(5) Å, c=14.787(5) Å, α=100.388(5)°, β=106.555(5)°, γ=89.945(5)°, V=2195.7(14) Å$^3$, Z=2, $\rho_{calc}$=1.260 g/cm$^3$, R$_1$=0.0647 for 4018 reflections with I>2σ(I). The structure was determined to be a rotational twin, the twinning law being a two-fold rotation about the (0,1,1) reciprocal lattice direction.

Example 4

Irradiation of 2(5-OMe-res).2(poly-3-ene) to Provide [5]-Laddarane

A finely ground sample of 2(5-OMe-res).2(poly-3-ene) was placed between two pyrex plates and irradiated with a 500 W Hg lamp. The sample was turned in eight hour intervals to ensure uniform irradiation over a period of 72 hours to provide the [5]-ladderane in 100% conversion. $^1$H NMR of irradiated 2(5-OMe-res).2(poly-3-ene) (300 MHz, DMSO-d$_6$): δ=9.15 (br. s, 4H), 8.25 (dd, 8H), 7.02 (dd, 8H), (br. t, 2H), 5.78 (br. d, 4H), 4.27 (br. s, 4H), 3.61 (s, 6H), 3.27 (br. s, 4H), 3.12 (br. s, 4H). Stirring of the irradiated solid with 1M KOH solution, followed by extraction with methylene chloride and evaporation of the organic phase, yielded the [5]-ladderane as a white solid in 85% yield. Crystal data for the [5]-ladderane.2(benzene): monoclinic, P 2$_1$/c, a=9.475(2) Å, b=15.048(3) Å, c=12.235(2) Å, β=95.95(3)°, V=1735.0(6) Å$^3$, Z=4, $\rho_{calc}$=1.196 g/cm$^3$, R$_1$=0.0438 for 1625 reflections with I>2σ(I).

The procedures described in examples 1-4 were readily scaled up to give the ladderanes in gram quantities. Single crystals of the [3]-ladderane were grown from ethanol, while single crystals of [5]-ladderane were grown from benzene yielding a 1:2 benzene solvate.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a ladderane comprising, associating two or more polyene molecules with a template such that the polyene molecules are properly aligned to allow for formation of the ladderane, and reacting the polyene molecules under conditions suitable to provide the ladderane.

2. The method of claim 1 where the polyene molecules and the template are associated by dipole-dipole interactions or by van der Waals forces.

3. The method of claim 1 where the polyene molecules and the template are associated by coordination.

4. The method of claim 3 where the polyene molecules and the template are associated by hydrogen bonds.

5. The method of claim 1 wherein each of the polyene molecules comprises 3-20 double bonds.

6. The method of claim 1 wherein each of the polyene molecules comprises 3-10 double bonds.

7. The method of claim 1 wherein each of the polyene molecules comprises 3-6 double bonds.

8. The method of claim 1 wherein each polyene comprises only trans double bonds.

9. The method of claim 1 wherein each polyene independently comprises 6-40 carbon atoms.

10. The method of claim 1 wherein each polyene independently comprises 6-30 carbon atoms.

11. The method of claim 1 wherein each polyene independently comprises 6-20 carbon atoms.

12. The method of claim 1 wherein each polyene is terminally substituted with a group that is capable of associating with the template.

13. The method of claim 12 wherein each group independently comprises an amino nitrogen, a thiol, an alcohol, or a carboxylic acid.

14. The method of claim 13 wherein each group comprises an amino nitrogen.

15. The method of claim 14 wherein each group is a pyridine ring.

16. The method of claim 15 wherein each group is a 4-pyridine ring.

17. The method of claim 1 wherein the template is an inorganic molecule, an organic molecule, a solid support, or an assembly comprising inorganic or organic molecules or a mixture thereof held together by non-covalent bonds.

18. The method of claim 1 wherein the template is an inorganic molecule.

19. The method of claim 18 wherein the inorganic molecule is a transition metal complex.

20. The method of claim 1 wherein the template is an organic molecule.

21. The method of claim 20 wherein the organic molecule is a polyol, a poly-ether, or a polyamine.

22. The method of claim 20 wherein the organic molecule comprises an aromatic ring.

23. The method of claim 22 wherein the aromatic ring is 1,3 substituted with groups capable of associating with the polyene molecules.

24. The method of claim 22 wherein the organic molecule comprises a 1,3-substituted phenyl ring or a 1,3-substituted naphthyl ring.

25. The method of claim 22 wherein the organic molecule comprises a 1,3-dihydroxy substituted phenyl ring or a 1,3-dihydroxy substituted naphthyl ring.

26. The method of claim 22 wherein the organic molecule is resorcinol, orcinol, 4-ethylresorcinol, 4-hexylresorcinol, olivetol, 4-cyclohexylresorcinol, 4-benzylresorcinol, 4-chlororesorcinol, 4-bromoresorcinol, 4,6-dichlororesorcinol, 4,6-dibromoresorcinol, 4,6-di-tert-butylresorcinol, 4,6-di-(1,1-diphenylethyl)resorcinol, 3,5-dihydroxybenzaldehyde, 5-cyanoresorcinol, 5-acetylresorcinol, 5-methoxyresorcinol, 5-carboxymethylresorcinol, 1,3-dihydroxynaphthalene, 4,6-dibromo-5-carboxymethylresorcinol, 2,4,6-trihydroxybenzaldehyde, methyl 2,4-6-trihydroxyphenyl ketone, ethyl 2,4-6-trihydroxyphenyl ketone, propyl 2, 4-6-trihydroxyphenyl ketone, butyl 2,4-6-trihydroxyphenyl ketone, pentyl 2,4-6-trihydroxyphenyl ketone, hexyl 2,4-6-trihydroxyphenyl ketone, or phenyl 2,4-6-trihydroxyphenyl ketone.

27. The method of claim 1 wherein each double bond of one polyene is aligned within about 3.2 to about 4.5 Angstroms of a double bond on another polyene to allow for formation of the ladderane.

28. The method of claim 1 wherein each double bond of one polyene is aligned within less than about 4.2 Angstroms of a double bond on another polyene to allow for formation of the ladderane.

29. The method of claim 1 wherein the reacting is carried out in a solid state.

30. The method of claim 1 wherein the reacting is carried out by treating the polyenes with light or heat or a combination thereof.

31. A method for preparing a ladderane comprising, 1) associating two or more polyene molecules with a template, 2) forming a solid comprising the template and the polyene molecules, wherein the polyene molecules are properly aligned within the solid to allow for formation of the ladderane, and 3) reacting the polyene molecules under conditions suitable to provide the ladderane.

32. A method for preparing a ladderane comprising, 1) associating two or more polyene molecules with a template comprising two hydroxyl groups, 2) forming a solid comprising the template and the polyene molecules, wherein the polyene molecules are properly aligned within the solid to allow for formation of the ladderane, and 3) reacting the polyene molecules under conditions suitable to provide the ladderane.

33. A method for preparing a ladderane comprising, 1) associating two polyene molecules that each comprise an amino nitrogen with a template comprising two hydroxyl groups, 2) forming a solid comprising the template and the polyene molecules, wherein the polyene molecules are properly aligned within the solid to allow for formation of the ladderane, and 3) reacting the polyene molecules under conditions suitable to provide the ladderane.

34. A method for preparing a ladderane comprising, 1) associating two polyene molecules that each comprise a pyridine ring with a template comprising a 1,3-dihydroxy substituted phenyl ring, 2) forming a solid comprising the template and the polyene molecules, wherein the polyene molecules are properly aligned within the solid to allow for formation of the ladderane, and 3) reacting the polyene molecules under conditions suitable to provide the ladderane.

35. A method for preparing a ladderane comprising, 1) combining polyene molecules that comprise a pyridine ring with template molecules that comprise a 1,3-dihydroxy substituted phenyl ring in a solvent, 2) allowing a crystalline solid that comprises the template molecules and the polyene molecules to form, wherein the polyene molecules are properly aligned within the crystalline solid to allow for formation of the ladderane, and 3) irradiating the solid under conditions suitable to provide the ladderane.

36. The method of claim 31 wherein the ladderane is an [n]-3, [n]-5, [n]-7, [n]-9, or [n]-11 ladderane.

37. The method of claim 31 wherein the polyene is 1,4-bis(4-pyridyl)-1,3-butadiene or 1,6-bis(4-pyridyl)-1,3,5-hexatriene.

38. The method of claim 31 wherein the template comprises a 1,3-dihydroxybenzene.

* * * * *